United States Patent
Bradley et al.

(10) Patent No.: US 6,861,564 B2
(45) Date of Patent: Mar. 1, 2005

(54) PROCESS FOR PREPARING RESORCINOL DERIVATIVES

(75) Inventors: Stuart Edward Bradley, Birmingham (GB); John Kitchin, Middlesex (GB); Graham Michael Wynne, Walsall (GB)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 10/282,201

(22) Filed: Oct. 28, 2002

(65) Prior Publication Data

US 2003/0088113 A1 May 8, 2003

Related U.S. Application Data

(62) Division of application No. 09/801,999, filed on Mar. 8, 2001, now Pat. No. 6,504,037.
(60) Provisional application No. 60/189,704, filed on Mar. 15, 2000.

(51) Int. Cl.$^7$ ............................................. C07C 49/105
(52) U.S. Cl. ...................................................... 568/377
(58) Field of Search ...................... 549/341; 568/377, 568/306; 560/144; 564/163

(56) References Cited

U.S. PATENT DOCUMENTS 6,229,025 B1    5/2001   Hawkins .................... 549/397

FOREIGN PATENT DOCUMENTS

WO    0056702    9/2000

OTHER PUBLICATIONS

European Search Report, EP 01301995.5.
Stork and Danheiser, "The Regiospecific Alkylation of Cyclic β Diketone Enol Ethers. A General Synthesis of 4–Alkylcyclohexenones", *J. Org. Chem.*, vol. 38, No. 9, 1973, pp. 1775–1776.
Stealey et al., "A Convenient Synthesis of 2–Alkyl–Mono–O–Alkylated and 2–Alkyl Resorcinols", *Synthetic Communications*, vol. 20, No. 12, 1990, pp. 1869–1876.
James L. Dye, et al., "The Regiospecific Alkylation of Cyclic B Diketone Enol Ethers. A General Synthesis of 4–Alkylcycolohexenones", J. Org. Chem., vol. 38, No. 9, 1973.
M. A. Stealy, et al., "A Convenient Synthesis of 2–alkyl–mono–o–alkylated And 2–alkyl Resorcinols", Synthetic Communications, 20(12), pp 1869–1876, 1990.

*Primary Examiner*—Johann Richter
*Assistant Examiner*—Ebenezer Sackey
(74) *Attorney, Agent, or Firm*—Rosanne Goodman

(57) ABSTRACT

The present invention relates to an improved process for preparing 4-substituted resorcinol derivatives, and intermediate compounds useful in the preparation of such resorcinol derivatives.

7 Claims, No Drawings

PROCESS FOR PREPARING RESORCINOL DERIVATIVES

This application is a division of U.S. Ser. No. 09/801,999, filed Mar. 8, 2001, now U.S. Pat. No. 6,504,037 and claims benefit of provisional application 60/189,704, filed Mar. 15, 2000.

FIELD OF THE INVENTION

The present invention relates to an improved process for preparing 4-substituted resorcinol derivatives.

BACKGROUND OF THE INVENTION

Resorcinol derivatives are known to be useful for a variety of purposes. For example, in the cosmetic field, resorcinol derivatives have been used as skin lightening agents. The use of resorcinol derivatives as skin lightening agents is described in European Patent Application EP 904,774, published Mar. 31, 1999; U.S. Pat. No. 5,468,472, issued Nov. 21, 1995; U.S. Pat. No. 5,399,785, issued Mar. 21, 1995; European Patent Application EP 623,339, published Nov. 9, 1994; JP 5-4905, published Jan. 14, 1993; and European Patent Application EP 341,664, published Nov. 15, 1989.

Resorcinol derivatives have also been used as dandruff control agents (JP 4-169516, published Jun. 17, 1992); as anti-acne agents (JP 4-169511, published Jun. 17, 1992); as potentiators of anti-microbial compounds (U.S. Pat. No. 4,474,748, issued Oct. 2, 1984); as anti-browning agents for foods (U.S. Pat. No. 5,304,679, issued Apr. 19, 1994); and in the preparation of photographic dye images (U.S. Pat. No. 3,756,818, issued Sep. 4, 1973).

The present invention provides an improved process for preparing 4-substituted resorcinol derivatives. The present invention further provides intermediate compounds useful in preparing such resorcinol derivatives, as well as processes for preparing the intermediate compounds. The improved process of the present invention is easier to use than standard methods for preparing resorcinol derivatives in large quantities. In addition, the improved process of the present invention results in a higher yield of final product than standard methods.

SUMMARY OF INVENTION

The invention provides a process for preparing a resorcinol derivative of formula I:

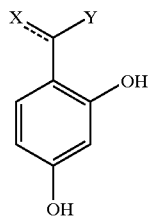

or a pharmaceutically acceptable salt thereof, wherein the dashed line indicates an optional double bond at that position, and wherein X and Y are each independently selected from hydrogen, $(C_1-C_{12})$alkyl, $(C_2-C_{12})$alkenyl, $(C_2-C_{12})$alkynyl, or X and Y are taken together with the carbon to which they are attached to form a $(C_4-C_8)$ cycloalkyl ring or $(C_5-C_8)$cycloalkenyl ring, provided that the $(C_4-C_8)$cycloalkyl ring or $(C_5-C_8)$cycloalkenyl ring is not aromatic; which $(C_1-C_{12})$alkyl, $(C_2-C_{12})$alkenyl, $(C_2-C_{12})$alkynyl, $(C_4-C_8)$cycloalkyl ring or $(C_5-C_8)$ cycloalkenyl ring is optionally substituted by one to three independently selected groups Z, wherein Z is any substituent capable of being substituted thereon where the process of the present invention can be used to prepare the particular substituted resorcinol derivative.

In a preferred embodiment, Z is selected from the group consisting of cyano; halo; $(C_1-C_6)$alkyl; aryl; $(C_2-C_9)$ heterocycloalkyl; $(C_2-C_9)$heteroaryl; aryl$(C_1-C_6)$alkyl-; =O; =CHO$(C_1-C_6)$alkyl; amino; hydroxy; $(C_1-C_6)$ alkoxy; aryl$(C_1-C_6)$alkoxy-; $(C_1-C_6)$acyl; $(C_1-C_6)$ alkylamino-; aryl$(C_1-C_6)$alkylamino-; amino$(C_1-C_6)$alkyl-; $(C_1-C_6)$alkoxy—CO—NH—; $(C_1-C_6)$alkylamino-CO—; $(C_2-C_6)$alkenyl; $(C_2-C_6)$alkynyl; hydroxy$(C_1-C_6)$alkyl-; $(C_1-C_6)$alkoxy$(C_1-C_6)$alkyl-; $(C_1-C_6)$acyloxy$(C_1-C_6)$ alkyl-; nitro; cyano$(C_1-C_6)$alkyl-; halo$(C_1-C_6)$alkyl-; nitro $(C_1-C_6)$alkyl-; trifluoromethyl; trifluoromethyl$(C_1-C_6)$ alkyl-; $(C_1-C_6)$acylamino-; $(C_1-C_6)$acylamino$(C_1-C_6)$ alkyl-; $(C_1-C_6)$alkoxy$(C_1-C_6)$acylamino-; amino$(C_1-C_6)$ acyl-; amino$(C_1-C_6)$acyl$(C_1-C_6)$alkyl-; $(C_1-C_6)$alkylamino $(C_1-C_6)$acyl-; $((C_1-C_6)$alkyl$)_2$amino$(C_1-C_6)$acyl-; —$CO_2R^2$; —$(C_1-C_6)$alkyl-$CO_2R^2$; —$C(O)N(R^2)_2$; —$(C_1-C_6)$alkyl-$C(O)N(R^2)_2$; $R^2ON=$; $R^2ON=(C_1-C_6)$ alkyl-; $R^2ON=CR^2(C_1-C_6)$alkyl-; —$NR^2(OR^2)$; —$(C_1-C_6)$alkyl-$NR^2(OR^2)$; —$C(O)(NR^2OR^2)$; —$(C_1-C_6)$ alkyl-$C(O)(NR^2OR^2)$; —$S(O)_mR^2$; wherein each $R^2$ is independently selected from hydrogen, $(C_1-C_6)$alkyl, aryl, or aryl$(C_1-C_6)$alkyl-; $R^3C(O)O$—, wherein $R^3$ is $(C_1-C_6)$alkyl, aryl, or aryl$(C_1-C_6)$alkyl-; $R^3C(O)O$—$(C_1-C_6)$alkyl-; $R^4R^5N$—$C(O)$—$O$—; $R^4R^5NS(O)_2$—; $R^4R^5NS(O)_2$ $(C_1-C_6)$alkyl-; $R^4S(O)_2R^5N$—; $R^4S(O)_2R^5N(C_1-C_6)$alkyl-; wherein m is 0, 1 or 2, and $R^4$ and $R^5$ are each independently selected from hydrogen or $(C_1-C_6)$alkyl; —$C(=NR^6)(N (R^4)_2)$; —$(C_1-C_6)$alkyl-$C(=NR^6)(N(R^4)_2)$ wherein $R^6$ represents $OR^2$ or $R^2$ wherein $R^2$ is defined as above; —OC (O)aryl$(C_1-C_6)$alkyl; —NH$(C_1-C_6)$alkyl; aryl$(C_1-C_6)$ alkyl-HN—; and a ketal.

The present invention also provides various intermediate compounds useful in this process, and methods for making them. Specifically, this invention relates to a process for preparing a compound of formula (6)

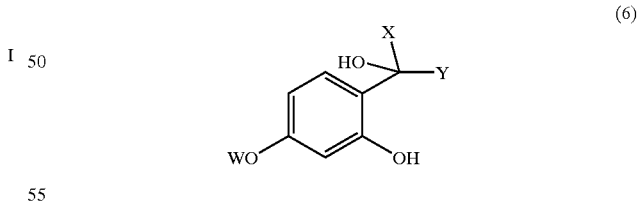

wherein W is hydrogen or a protecting group;

wherein X and Y are each independently selected from hydrogen, $(C_1-C_{12})$alkyl, $(C_2-C_{12})$alkenyl, $(C_2-C_{12})$ alkynyl, or X and Y are taken together with the carbon to which they are attached to form a $(C_4-C_8)$cycloalkyl ring or $(C_5-C_8)$cycloalkenyl ring, provided that the $(C_4-C_8)$ cycloalkyl ring or $(C_5-C_8)$cycloalkenyl ring is not aromatic; and wherein the $(C_1-C_{12})$alkyl, $(C_2-C_{12})$alkenyl, $(C_2-C_{12})$ alkynyl, $(C_4-C_8)$cycloalkyl ring or $(C_5-C_8)$cycloalkenyl ring is optionally further substituted by one to three independently selected groups Z, where Z is as defined above;

comprising reacting a compound of formula (5)

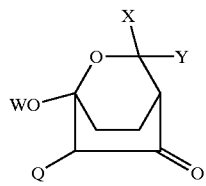
(5)

wherein Q is halo, with a base to form the compound of formula (6). In a preferred embodiment, Q is bromo, iodo or chloro; more preferably Q is bromo or iodo; and most preferably Q is bromo.

The present invention further provides a process for preparing a compound of formula (7)

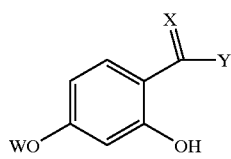
(7)

wherein W, X and Y are as defined above;
comprising reacting a compound of formula (5)

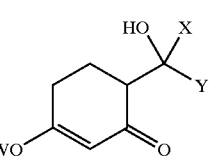
(5)

wherein Q is as defined above, with a base to form the compound of formula (7).

In a preferred embodiment, the compound of formula (5) is prepared by reacting the compound of formula (4)

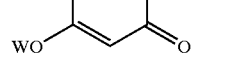
(4)

wherein W, X and Y are as defined above, with a halogenating agent, wherein the halogen corresponds to Q in the compound of formula (5). In a preferred embodiment, Q is bromo, and the compound of formula (5) is prepared by reacting the compound of formula (4) with a brominating agent such as, e.g., N-bromosuccinimide.

In a further preferred embodiment, the compound of formula (4) is prepared by reacting a compound of formula (2)

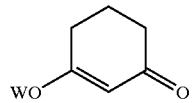
(2)

with a compound of formula (3)

(3)

wherein W, X and Y are as defined above, in the presence of a base to form the compound of formula (4).

The present invention further provides a process for preparing a compound of formula (5)

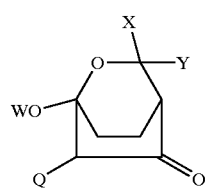
(5)

wherein Q, W, X and Y are as defined above, comprising reacting the compound of formula (4)

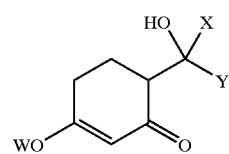
(4)

with a halogenating agent, as described above, to form the compound of formula (5).

In a preferred embodiment, the compound of formula (4) is prepared by reacting a compound of formula (2)

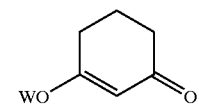
(2)

with a compound of formula (3)

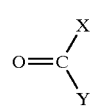
(3)

wherein W, X and Y are as defined above, in the presence of a base to form the compound of formula (4).

The present invention further provides a process for preparing a compound of formula (4)

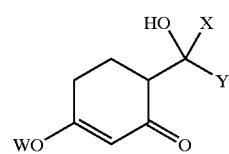
(4)

wherein W, X and Y are as defined above; comprising reacting a compound of formula (2)

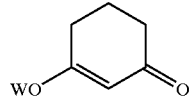
(2)

with a compound of formula (3)

(3)

in the presence of a base to form the compound of formula (4).

The present invention further provides a process for preparing a compound of formula I(a)

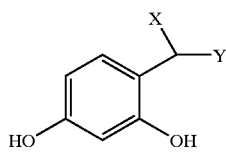
I(a)

wherein X and Y are defined as above, comprising:

(a) reacting a compound of formula (5)

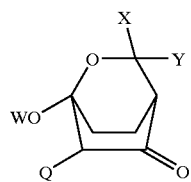
(5)

wherein Q is halo, W is hydrogen or a protecting group, and X and Y are as defined above, with a base to form a compound of formula (6); and

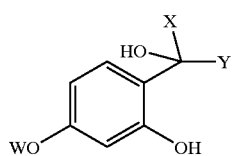
(6)

(b) where W is H, reducing the compound of formula (6) so formed to form the compound of formula I(a); or (c) where W is a protecting group, reducing the compound of formula (6) so formed and removing the protecting group to form the compound of formula I(a).

In a preferred embodiment, the compound of formula (6) is reduced to form the compound of formula I(a) by reaction with triethysilane in the presence of a Lewis acid, or alternatively by hydrogenation under standard conditions.

The present invention further provides a process for preparing a compound of formula I(a)

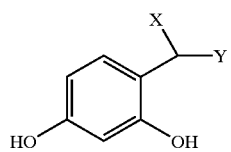
I(a)

wherein X and Y are as defined above; comprising:

(a) reacting a compound of formula (5)

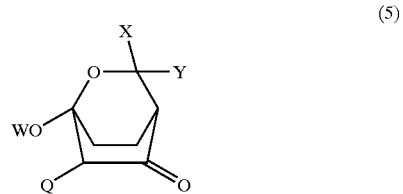
(5)

wherein Q is halo, W is hydrogen or a protecting group, and X and Y are as defined above, with a base to form a compound of formula (7); and

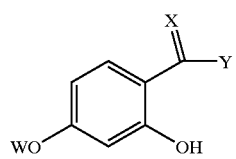
(7)

(b) where W is H, hydrogenating the compound of formula (7) so formed to form the compound of formula I(a); or (c) where W is a protecting group, hydrogenating the compound of formula (7) so formed and removing the protecting group to form the compound of formula I(a).

The present invention further provides a process for preparing a compound of formula I(a)

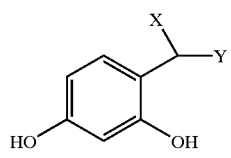
I(a)

wherein X and Y are defined as above; comprising:

(a) reacting a compound of formula (5)

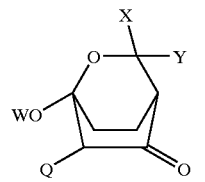
(5)

wherein Q is halo, W is hydrogen or a protecting group, and X and Y are as defined above, with a base to form a compound of formula (6);

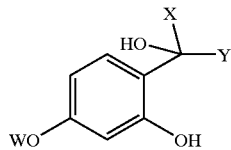
(6)

(b) reacting the compound of formula (6) so formed with a base to form a compound of formula (7); and

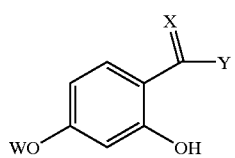
(7)

(c) where W is H, hydrogenating the compound of formula (7) so formed to form the compound of formula I(a); or (d) where W is a protecting group, hydrogenating the compound of formula (7) so formed and removing the protecting group to form the compound of formula I(a).

The present invention further provides a process for preparing a compound of formula I(a)

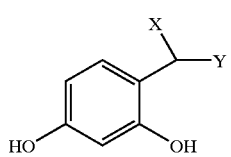
I(a)

wherein X and Y are as defined above; comprising:

(a) reacting a compound of formula (5)

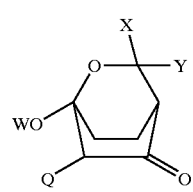
(5)

wherein Q is halo, W is hydrogen or a protecting group, and X and Y are as defined above, with a base to form a compound of formula (6);

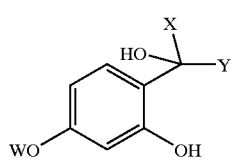
(6)

(b) reacting the compound of formula (6) so formed with a base to form a compound of formula (7); and

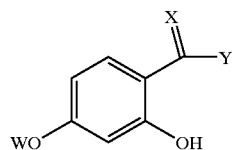
(7)

(c) where W is H, hydrogenating the compound of formula (7) so formed to form the compound of formula I(a); or d) where W is a protecting group, removing the protecting group from compound (7) so formed to form the compound of formula I(b)

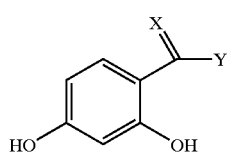
I(b)

and hydrogenating the compound of formula I(b) so formed to form the compound of formula I(a).

The present invention further provides a process for preparing a compound of formula I(a)

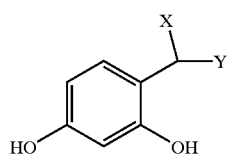
I(a)

wherein X and Y are as defined above; comprising:

(a) reacting a compound of formula (5)

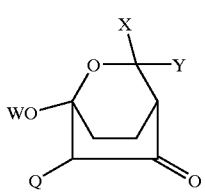
(5)

wherein Q is halo, W is hydrogen or a protecting group, and X and Y are as defined above, with a base to form a compound of formula (7); and

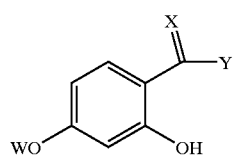
(7)

(b) where W is H, hydrogenating the compound of formula (7) so formed to form the compound of formula I(a); or (c) where W is a protecting group, removing the protecting group from compound (7) so formed to form the compound of formula I(b)

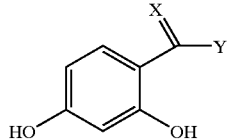

and hydrogenating the compound of formula I(b) so formed to form the compound of formula I(a).

The present invention further comprises a process for preparing a compound of formula I(b)

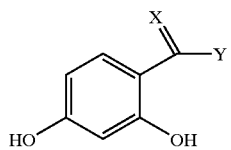

wherein X and Y are as defined above; comprising:

(a) reacting a compound of formula (5)

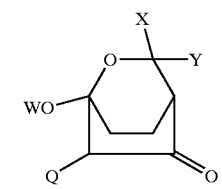

wherein Q is halo, W is hydrogen or a protecting group, and X and Y are as defined above, with a base to form a compound of formula (6);

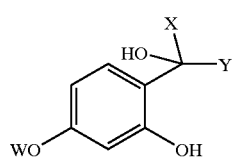

(b) reacting the compound of formula (6) so formed with a base to form a compound of formula I(b) when W is H, and a compound of formula (7) when W is a protecting group; and

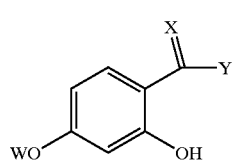

(c) when W is a protecting group, removing the protecting group from the compound of formula (7) so formed to form the compound of formula I(b).

The present invention further provides a process for preparing a compound of formula I(b)

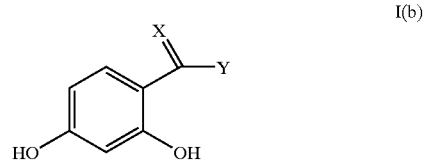

wherein X and Y are defined as above; comprising:

(a) reacting a compound of formula (5)

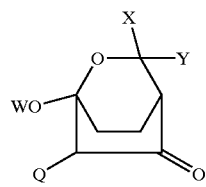

wherein Q is halo, W is hydrogen or a protecting group, and X and Y are as defined above, with a base to form a compound of formula I(b) when W is H, and a compound of formula (7) when W is a protecting group; and

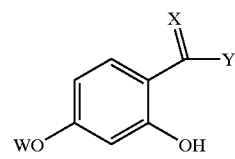

(b) when W is a protecting group, removing the protecting group from the compound of formula (7) so formed to form the compound of formula I(b).

As explained below in the description of Scheme I, where W is H, the compound of formula (5) can exist in equilibrium with the compound of formula (5') as follows.

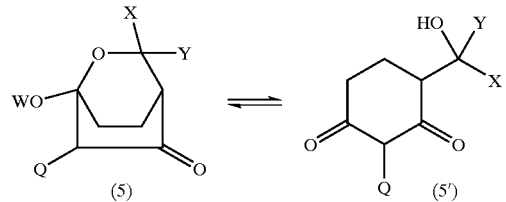

where W is H, the compound of formula (5') may be formed directly from the compound of formula (4). In all of the processes described herein where W is H, where the compound of claim (5) is utilized, the compound of claim (5') can be utilized in its place under the same reaction conditions as recited, e.g., to prepare the compounds of formula (6) or (7). The present invention also provides a process for preparing the compound of formula (5') by treating the compound of formula (4), where W is H, with a halogenating agent to form the compound of formula (5').

The various processes of the present invention, as described above, are incorporated into Scheme 1, shown below.

In a preferred non-limiting embodiment, X and Y are taken together with the carbon to which they are attached to form a ($C_5$–$C_8$)cycloalkyl ring or a ($C_5$–$C_8$)cycloalkenyl ring having the following structure:

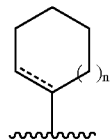

wherein n is 0, 1, 2 or 3, where such ($C_5$–$C_8$)cycloalkyl ring or ($C_5$–$C_8$)cycloalkenyl ring is optionally substituted, and wherein the dashed line indicates an optional double bond at that position. In a non-limiting embodiment, the ($C_5$–$C_8$) cycloalkyl ring or ($C_5$–$C_8$)cycloalkenyl ring is substituted by one to three independently selected groups Z as defined above.

In a preferred embodiment, X and Y are taken together with the carbon to which they are attached to form a cyclohexyl or cyclohexenyl ring, and most preferably a cyclohexyl ring.

In a further preferred embodiment, X and Y are taken together with the carbon to which they are attached to form a cyclopentyl or cyclopentenyl ring, and most preferably a cyclopentyl ring.

In a further preferred embodiment, the ($C_5$–$C_8$)cycloalkyl ring or ($C_5$–$C_8$)cycloalkenyl ring is not substituted.

In a further preferred embodiment, the ($C_5$–$C_8$)cycloalkyl ring or ($C_5$–$C_8$)cycloalkenyl ring is monosubstituted. More preferably, X and Y are taken together with the carbon to which they are attached to form a monosubstituted cyclohexyl or monosubstituted cyclopentyl ring.

In a further preferred embodiment, the ($C_5$–$C_8$)cycloalkyl ring or ($C_5$–$C_8$)cycloalkenyl ring is disubstituted. More preferably, X and Y are taken together with the carbon to which they are attached to form a disubstituted cyclohexyl or disubstituted cyclopentyl ring.

Where X and Y are taken together with the carbon to which they are attached to form a cyclohexyl or cyclohexenyl ring, the ring is preferably substituted at the 3- or 4-position, and more preferably at the 4-position.

Where X and Y are taken together with the carbon to which they are attached to form a cyclopentyl or cyclopentenyl ring, the ring is preferably substituted at the 3-position.

In a further preferred embodiment, X and Y are taken together with the carbon to which they are attached to form:

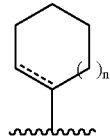

which is substituted with one to three independently selected groups Z as described above;
wherein n is 0, 1, or 2.

In a further preferred embodiment, n is 0 or 1.

In a further preferred embodiment, n is 0; and the dashed line represents a double bond at that position.

In a further preferred embodiment, n is 1.

In a further preferred embodiment, the ring formed by X and Y taken together with the carbon to which they are attached is substituted by OH, =O, =NOH, $CH_2OH$ or

or a combination thereof.

In a further preferred embodiment, n is 0; the ring formed by X and Y taken together with the carbon to which they are attached is substituted by =NOH; and the dashed line represents a double bond at that position.

In a further preferred embodiment, n is 1; and the ring formed by X and Y taken together with the carbon to which they are attached is substituted by OH, =O, =NOH, $CH_2OH$, or

or a combination thereof.

Where Z is a ($C_2$–$C_9$)heterocycloalkyl substituent, it is preferably a group of the formula:

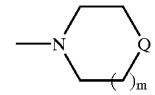

wherein m is 0, 1 or 2, and
Q is $CH_2$, $NR^2$, O, S, SO, or $SO_2$.

In a further preferred embodiment, X and Y are taken together with the carbon to which they are attached to form a cyclohexyl, cyclohexenyl, cyclopentyl or cyclopentenyl ring that is monosubstituted with Z selected from the group consisting of OH, $R^3C(O)O$—, $R^3C(O)O$—($C_1$–$C_6$)alkyl-, $R^2ON$=, $R^2ON$=($C_1$–$C_6$)alkyl-, $R^2ON$=$CR^2$($C_1$–$C_6$) alkyl-, —$NR^2(OR^2)$, $R^4S(O)_2R^5N$—, and $R^4S(O)_2R^5N$ ($C_1$–$C_6$)alkyl-; wherein $R^2$, $R^3$, $R^4$ and $R^5$ are as defined above.

In a further preferred embodiment, X and Y are taken together with the carbon to which they are attached to form a cyclohexyl or cyclopentyl ring that is monosubstituted with Z selected from the group consisting of OH, $R^3C(O)$ O—, $R^3C(O)O$—($C_1$–$C_6$)alkyl-, $R^2ON$=, $R^2ON$=($C_1$–$C_6$) alkyl-, $R^2ON$=$CR^2$($C_1$–$C_6$)alkyl-, —$NR^2(OR^2)$, $R^4S(O)_2$ $R^5N$—, and $R^4S(O)_2R^5N(C_1$–$C_6$)alkyl-; wherein $R^2$, $R^3$, $R^4$ and $R^5$ are as defined above.

In a further preferred embodiment, Z is OH.

In a further preferred embodiment, Z is $R^3C(O)O$—.

In a further preferred embodiment, Z is $R^3C(O)O$—($C_1$–$C_6$)alkyl-.

In a further preferred embodiment, Z is $R^2ON$=, $R^2ON$=($C_1$–$C_6$)alkyl-, or $R^2ON$=$CR^2$($C_1$–$C_6$)alkyl-.

In a further preferred embodiment, Z is $R^2ON$=.

In a further preferred embodiment, Z is —$NR^2(OR^2)$.

In a further preferred embodiment, Z is $R^4S(O)_2R^5N$—.

In a further preferred embodiment, Z is $R^4S(O)_2R^5N$ ($C_1$–$C_6$)alkyl-.

In a non-limiting embodiment, the process of the present invention can be used to prepare a compound selected from the group consisting of:

4-cyclohexyl resorcinol;
4-cyclopentyl resorcinol;
4-(2,4-dihydroxyphenyl)cyclohexanol;
4-(2,4-Dihydroxyphenyl)cyclohexanone;
4-(2,4-Dihydroxyphenyl)cyclohexanone oxime;
O-Methyl-4-(2,4-dihydroxyphenyl)cyclohexanone oxime;

O-Benzyl-4-(2,4-dihydroxyphenyl)cyclohexanone oxime;
3-(2,4-dihydroxyphenyl)-2-cyclohexen-1-one;
(±)-3-(2,4-Dihydroxyphenyl)cyclohexanone;
3-(2,4-Dihydroxyphenyl)-2-cyclohexen-1-one oxime;
(±)-3-(2,4-Dihydroxyphenyl)cyclohexanone oxime;
(±)-4-[3-(1-Piperazinyl)cyclohexyl]-1,3-benzenediol;
(±)-N-[3-(2,4-Dihydroxyphenyl)cyclohexyl] methanesulfonamide;
(±)-4-[3-(Hydroxymethyl)cyclohexyl]-1,3-benzenediol;
(±)-4-[3-(Hydroxyamino)cyclohexyl]-1,3-benzenediol;
cis/trans-4-[4-(Hydroxymethyl)cyclohexyl]-1,3-benzenediol;
cis/trans-4-(4-Hydroxy-4-methylcyclohexyl)-1,3-benzenediol;
(±)-O-Methyl-3-(2,4-dihydroxyphenyl)cyclohexanone oxime;
(±)-3-(2,4-Dihydroxyphenyl)-1-methylcyclohexanol;
(±)-O-Benzyl-3-(2,4-dihydroxyphenyl)cyclohexanone oxime;
3-(2,4-Dihydroxyphenyl)-2-cyclopentenone oxime;
(±)-3-(2,4-Dihydroxyphenyl)cyclopentanone;
(±)-3-(2,4-Dihydroxyphenyl)cyclopentanone oxime;
4-(2,4-Dihydroxyphenyl)-3-cyclohexen-1-one;
cis/trans-N-[4-(2,4-Dihydroxyphenyl)cyclohexyl] acetamide;
cis-N-[4-(2,4-Dihydroxyphenyl)cyclohexyl]-1-butanesulfonamide;
trans-N-[4-(2,4-Dihydroxyphenyl)cyclohexyl] methanesulfonamide;
cis-N-[4-(2,4-Dihydroxyphenyl)cyclohexyl] methanesulfonamide;
4-[4-(4-Hydroxyphenyl)cyclohexyl]-1,3-benzenediol;
cis/trans-Methyl[4-(2,4 -dihydroxyphenyl)cyclohexyl] acetate;
trans-Methyl[4-(2,4-dihydroxyphenyl)cyclohexyl] acetate;
cis-Methyl[4-(2,4-dihydroxyphenyl)cyclohexyl]acetate;
trans-[4-(2,4-Dihydroxyphenyl)cyclohexyl]acetic acid;
cis-[4-(2,4-Dihydroxyphenyl)cyclohexyl]acetic acid;
cis/trans-[4-2,4-Dihydroxyphenyl)cyclohexyl]acetic acid;
cis/trans-[4-(2,4-Dihydroxyphenyl)cyclohexyl] acetonitrile;
cis/trans-4-[4-(2-Aminoethyl)cyclohexyl]-1,3-benzenediol;
(±)-4-(3,3-Difluorocyclohexyl)-1,3-benzenediol;
(±)-3-(2,4-Dihydroxyphenyl)cyclohexanecarboxamide;
(±)-3-(2,4-Dihydroxyphenyl)-N-hydroxycyclohexanecarboxamide;
(±)-3-(2,4-Dihydroxyphenyl)-N-ethylcyclohexanecarboxamide;
(±)-4-[3-Hydroxy-3-(hydroxymethyl)cyclohexyl]-1,3-benzenediol;
(±)-N-[3-(2,4-dihydroxyphenyl)cyclohexyl]acetamide;
trans-4-(2,4-Dihydroxyphenyl)cyclohexyl)4-(dimethylamino)benzoate;
cis/trans-4-(2,4-Dihydroxyphenyl) cyclohexanecarboxylic acid;
trans-4-(2,4-Dihydroxyphenyl)cyclohexyl ethylcarbamate;
trans-4-(2,4-Dihydroxyphenyl)cyclohexyl cyclohexylcarbamate;
trans-4-(2,4-Dihydroxyphenyl)cyclohexyl 4-tert-butylbenzoate;
trans-4-(2,4-Dihydroxyphenyl)cyclohexyl 4-fluorobenzoate;
trans-4-(2,4-Dihydroxyphenyl)cyclohexyl 4-trifluoromethylbenzoate;
trans-4-(2,4-Dihydroxyphenyl)cyclohexyl 4-methoxybenzoate;
trans-4-(2,4-Dihydroxyphenyl)cyclohexyl 4-methylbenzoate;
trans-4-(2,4-Dihydroxyphenyl)cyclohexyl 4-chlorobenzoate;
trans-4-(2,4-Dihydroxyphenyl)cyclohexyl 3,4-dimethylbenzoate;
trans-4-(2,4-Dihydroxyphenyl)cyclohexyl 3,4-dichlorobenzoate;
trans-4-[4-(Phenylsulfanyl)cyclohexyl]-1,3-benzenediol;
trans-4-[4-(Phenylsulfonyl)cyclohexyl]-1,3-benzenediol;
[4-(2,4-Dihydroxyphenyl)cyclohexyl]methyl propionate;
ethyl 4-(2,4-dihydroxyphenyl)-1-hydroxycyclohexane carboxylate;
cis/trans-4-[4-(hydroxyamino)cyclohexyl]-1,3-benzenediol;
trans-4-[4-(methoxyamino)cyclohexyl]-1,3-benzenediol; and a pharmaceutically acceptable salt thereof.

The term "resorcinol derivative", as used herein, refers to a compound comprising a resorcinol ring monosubstituted at the 4-position, as defined above, and is represented by the structure of formula I.

The term "alkyl", as used herein, unless otherwise indicated, includes saturated monovalent hydrocarbon radicals having straight, branched or cyclic moieties or combinations thereof, which may or may not be further substituted. Any substituents or functional groups on the alkyl group, as indicated herein, can be substituted anywhere on the alkyl group where such substitutions are possible.

The term "aryl", as used herein, refers to phenyl or naphthyl optionally substituted with one or more substituents, preferably from zero to two substituents, independently selected from halogen, OH, $(C_1-C_6)$alkyl, $(C_1-C_6)$ alkoxy, amino, $(C_1-C_6)$alkylamino, di-$((C_1-C_6)$ alkyl))amino, nitro, cyano and trifluoromethyl. Any substituents or functional groups on the aryl group, as indicated herein, can be substituted anywhere on the aryl group.

The term "one or more substituents", as used herein, refers to a number of substituents that equals from one to the maximum number of substituents possible based on the number of available bonding sites.

The "halo", as used herein, refers to halogen and, unless otherwise indicated, includes chloro, fluoro, bromo and iodo.

The term "acyl", as used herein, unless otherwise indicated, includes a radical of the general formula RCO wherein R is alkyl, alkoxy, aryl, arylalkyl, or arylalkyloxy and the terms "alkyl" or "aryl" are as defined above.

The term "acyloxy", as used herein, includes O-acyl groups wherein "acyl" is as defined above.

$(C_2-C_9)$Heterocycloalkyl, when used herein, refers to pyrrolidinyl, tetrahydrofuranyl, dihydrofuranyl, tetrahydropyranyl, pyranyl, thiopyranyl, aziridinyl, oxiranyl, methylenedioxyl, chromenyl, isoxazolidinyl, 1,3-oxazolidin-3-yl, isothiazolidinyl, 1,3-thiazolidin-3-yl, 1,2-pyrazolidin-2-yl, 1,3-pyrazolidin-1-yl, piperidinyl, thiomorpholinyl, 1,2-tetrahydrothiazin-2-yl, 1,3-tetrahydrothiazin-3-yl, tetrahydrothiadiazinyl, morpholinyl, 1,2-tetrahydrodiazin-2-yl, 1,3-tetrahydrodiazin-1-yl, tetrahydroazepinyl, piperazinyl, chromanyl, etc. One of ordinary skill in the art will understand that the connection of said ($C_2$–$C_9$)heterocycloalkyl ring can be through a carbon atom or through a nitrogen heteroatom where possible.

($C_2$–$C_9$)Heteroaryl, when used herein, refers to furyl, thienyl, thiazolyl, pyrazolyl, isothiazolyl, oxazolyl, isoxazolyl, pyrrolyl, triazolyl, tetrazolyl, imidazolyl, 1,3,5-oxadiazolyl, 1,2,4-oxadiazolyl, 1,2,3-oxadiazolyl, 1,3,5-thiadiazolyl, 1,2,3-thiadiazolyl, 1,2,4-thiadiazolyl, pyridyl, pyrimidyl, pyrazinyl, pyridazinyl, 1,2,4-triazinyl, 1,2,3-triazinyl, 1,3,5-triazinyl, pyrazolo[3,4-b]pyridinyl, cinnolinyl, pteridinyl, purinyl, 6,7-dihydro-5H-[l]pyridinyl, benzo[b]thiophenyl, 5, 6, 7, 8-tetrahydro-quinolin-3-yl, benzoxazolyl, benzothiazolyl, benzisothiazolyl, benzisoxazolyl, benzimidazolyl, thianaphthenyl, isothianaphthenyl, benzofuranyl, isobenzofuranyl, isoindolyl, indolyl, indolizinyl, indazolyl, isoquinolyl, quinolyl, phthalazinyl, quinoxalinyl, quinazolinyl, benzoxazinyl, etc. One of ordinary skill in the art will understand that the connection of said ($C_2$–$C_9$) heterocycloalkyl rings can be through a carbon atom or through a nitrogen heteroatom where possible.

Compounds of formula I may contain chiral centers and therefore may exist in different enantiomeric and diastereomeric forms. This invention relates to preparation of all optical isomers, stereoisomers and tautomers of the compounds of formula I, and mixtures thereof.

Formula I, as defined above, also includes compounds identical to those depicted but for the fact that one or more hydrogen, carbon or other atoms are replaced by isotopes thereof. Such compounds may be useful as research and diagnostic tools in metabolism pharmacokinetic studies and in binding assays.

The present invention also relates to preparation of the pharmaceutically acceptable acid addition and base addition salts of any of the aforementioned compounds of formula I. The acids which are used to prepare the pharmaceutically acceptable acid addition salts of the aforementioned base compounds of this invention are those which form non-toxic acid addition salts, i.e., salts containing pharmacologically acceptable anions, such as the hydrochloride, hydrobromide, hydroiodide, nitrate, sulfate, bisulfate, phosphate, acid phosphate, acetate, lactate, citrate, acid citrate, tartrate, bitartrate, succinate, maleate, fumarate, gluconate, saccharate, benzoate, methanesulfonate, ethanesulfonate, benzenesulfonate, p-toluenesulfonate and pamoate (i.e., 1,1-methylene-bis-(2-hydroxy-3-naphthoate)) salts.

The present invention also provides various intermediate compounds useful in the preparation of wide variety of resorcinol derivatives.

The present invention provides an intermediate compound of formula (4), where W, X and Y are as defined above.

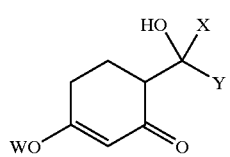

(4)

In a preferred embodiment, the intermediate compound of formula (4) has the structure of formula (4a),

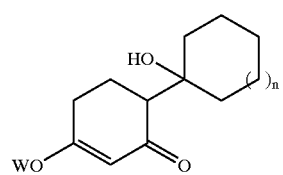

(4a)

where W is as defined above, and n is 0, 1, 2 or 3.

In a further preferred embodiment, the intermediate compound of formula (4) has the structure of formula (4b) or (4c),

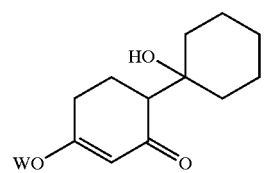

(4b)

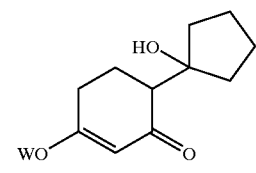

(4c)

where W is as defined above.

In a further preferred embodiment, the intermediate compound of formula (4) has the structure of formula (4d),

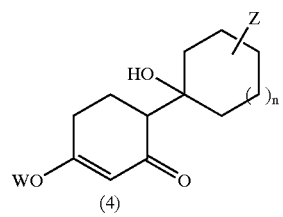

(4d)

(4)

where W and Z are as defined above, and n is 0, 1, 2 or 3.

In a further preferred embodiment, the intermediate compound of formula (4) has the structure of formula (4e) or (4f),

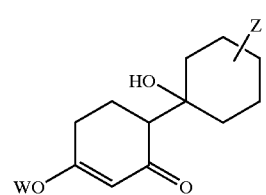

(4e)

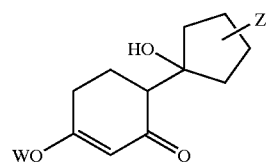

(4f)

where W and Z are as defined above.

In a further preferred embodiment, the intermediate compound of formula (4) has the structure of formula (4g),

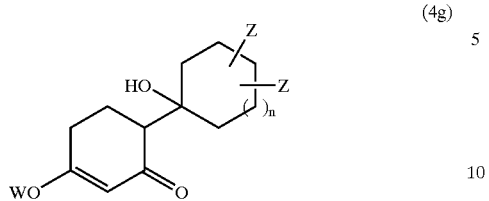
(4g)

where W and each Z are as defined above, and n is 0, 1, 2 or 3.

In a further preferred embodiment, the intermediate compound of formula (4) has the structure of formula (4h) or (4i),

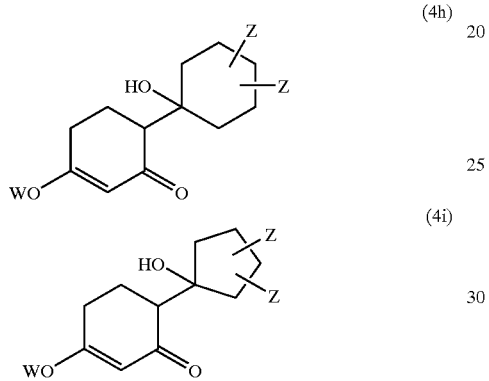
(4h)

(4i)

where W and each Z are as defined above.

The present invention further provides an intermediate compound of formula (5),

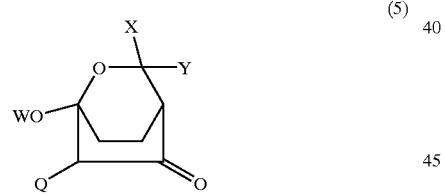
(5)

where Q, W, X and Y are as defined above.

In a preferred embodiment, the intermediate compound of formula (5) has the structure of formula (5a)

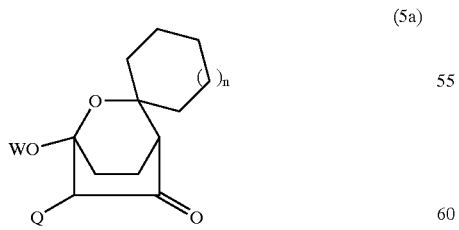
(5a)

wherein Q and W are as defined above, and n is 0, 1, 2, or 3.

In a further preferred embodiment, the intermediate compound of formula (5) has the structure of formula (5b) or (5c)

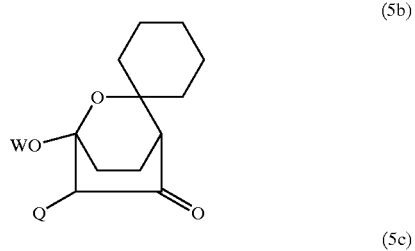
(5b)

(5c)

wherein Q and W are as defined above.

In a further preferred embodiment, the intermediate compound of formula (5) has the structure of formula (5d)

(5d)

wherein Q, W and Z are as defined above, and n is 0, 1, 2, or 3.

In a further preferred embodiment, the intermediate compound of formula (5) has the structure of formula (5e) or (5f), (5e)

(5f)

where Q, W and Z are as defined above.

In a further preferred embodiment, the intermediate compound of formula (5) has the structure of formula (5g)

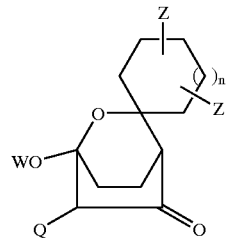

(5g)

wherein Q, W and Z are as defined above, and n is 0, 1, 2, or 3.

In a further preferred embodiment, the intermediate compound of formula (5) has the structure of formula (5h) or (5i),

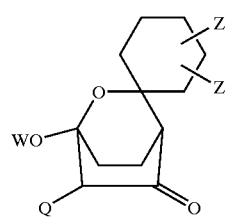

(5h)

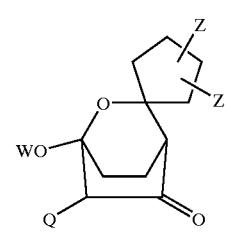

(5i)

wherein Q, W and each Z are as defined above.

The present invention further provides an intermediate compound of formula (5'),

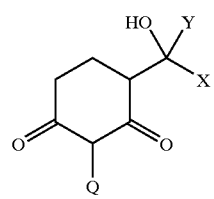

(5')

wherein Q, X and Y are as defined above.

In a preferred embodiment, the intermediate compound of formula (5') has the structure of formula (5'a),

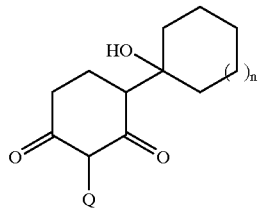

(5'a)

where Q is as defined above, and n is 0, 1, 2 or 3.

In a further preferred embodiment, the intermediate compound of formula (5') has the structure of formula (5'b) or (5'c),

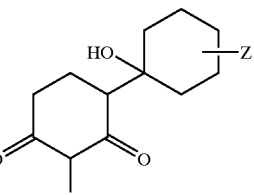

(5'b)

(5'c)

wherein Q is as defined above.

In a further preferred embodiment, the intermediate compound of formula (5') has the structure of formula (5'd) or (5'e),

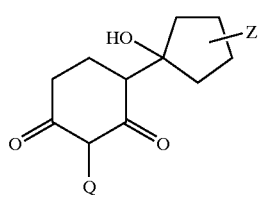

(5'd)

(5'e)

wherein Q and Z are as defined above.

In a further preferred embodiment, the intermediate compound of formula (5') has the structure of formula (5'f) or (5'g),
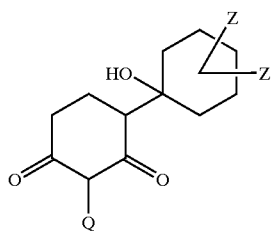
(5'f)
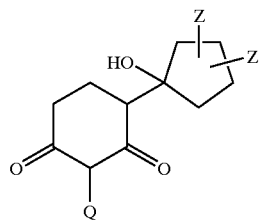
(5'g)
wherein Q and each Z are as defined above.
DETAILED DESCRIPTION OF THE INVENTION
The process of the present invention is described in the following reaction schemes and discussion.
Scheme 1
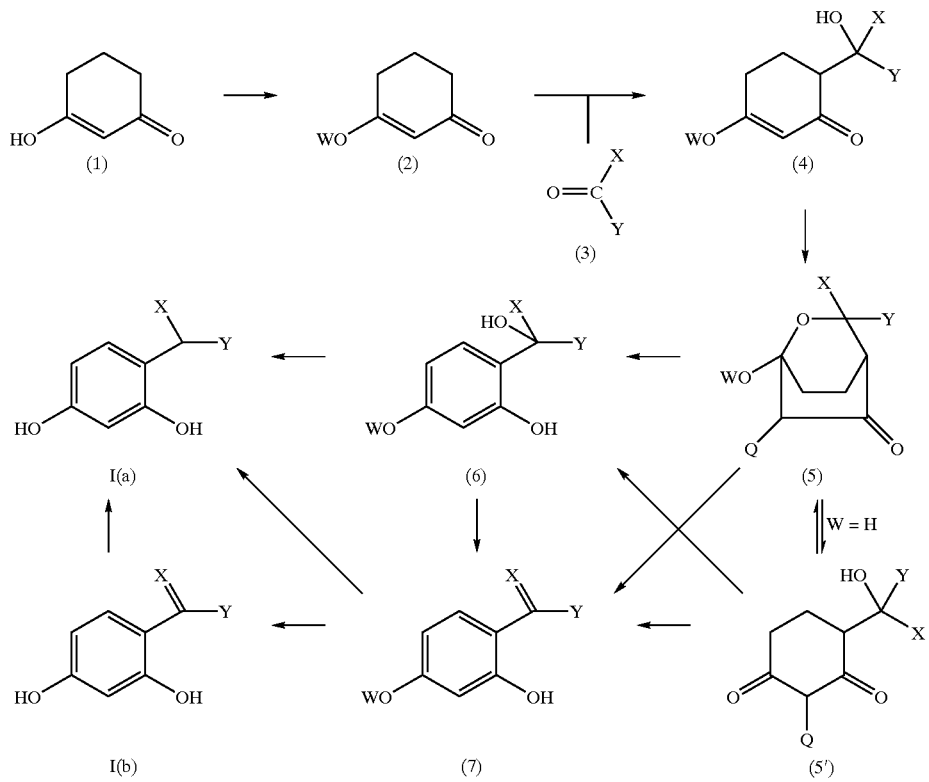
Scheme 2
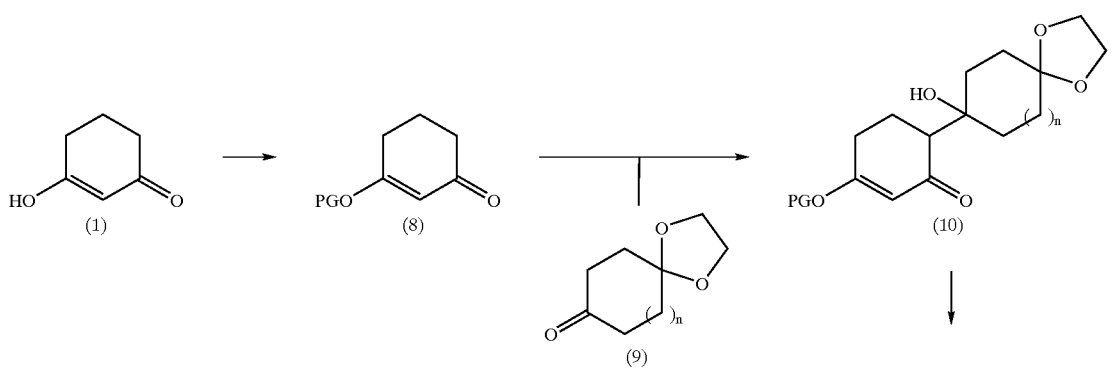

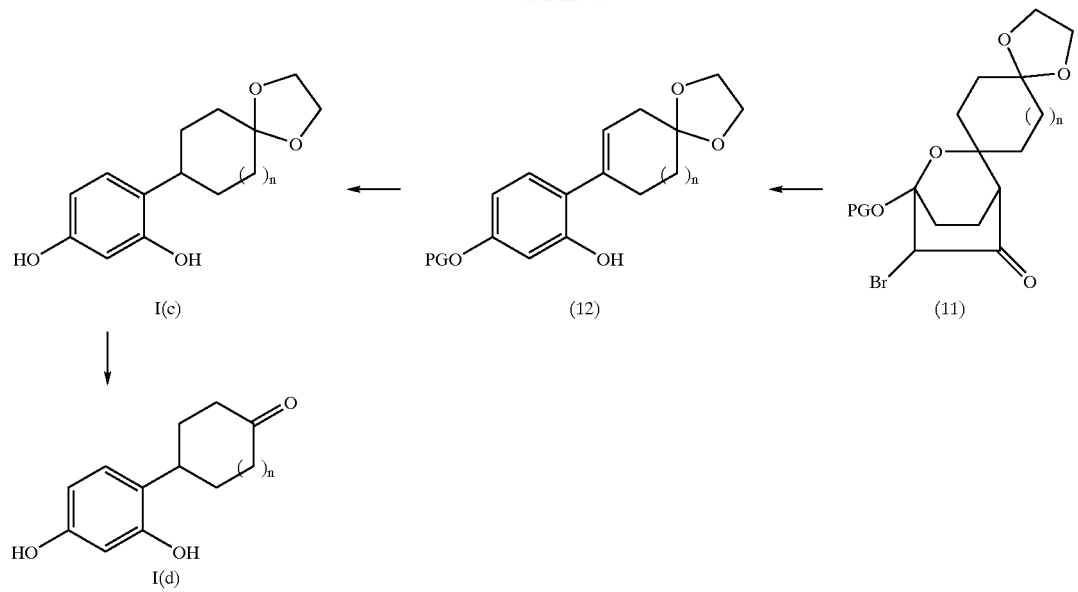

Referring to Scheme 1, compounds of formula (2) can be prepared starting with compound (1), which is commercially available (Aldrich Chemical Co.). A suitable protecting group can be selected as will be evident to those of skill in the art. An example of a suitable protecting group is benzyl. Conversion to compounds of formula (2) can occur under standard conditions. For instance, where the protecting group is benzyl, condensation can occur between compound (1) and benzyl alcohol with the removal of water using Dean-Stark apparatus. Condensation of compounds of formula (2) with compounds of formula (3) may occur using standard techniques, for instance, treatment of compounds of formula (2) with a base, such as lithium diisopropylamide or lithium hexamethyldisilazane, in an ethereal solvent followed by the addition of a compound of formula (3) would give compounds of formula (4). When W is H, condensation of compounds of formula (2) with compounds of formula (3) requires the use of at least two equivalents of a suitable base such as lithium diisopropylamide in an suitable solvent such as tetrahydrofuran, with a suitable co-solvent such as hexamethylphosphoramide. Treatment of compounds of formula (4) with a suitable halogenating reagent such as, for example, N-bromosuccinimide in a chlorinated solvent, such as dichloromethane or chloroform, at about room temperature, can give compounds of formula (5) where Q is halo, and preferably bromo. Where W is H, the compound of formula (5) may exist in equilibrium with the compound of formula (5'). Alternatively, where W is H, compounds of formula (5') may be prepared directly from compounds of formula (4) by treatment of the compound of formula (4) with a suitable halogenating agent. The process of the present invention is intended to encompass each of these various synthesis routes.

Compounds of formula (6) may then be generated from compounds of formula (5) or (5') under suitable conditions. Such conditions may involve treating compounds of formula (5) or (5') with a base such as, e.g., 1,8-diazobicyclo[5.4.0]undec-7-ene in a suitable solvent such as N,N-dimethylformamide at about room temperature. Compounds of formula I(a) may be generated using standard techniques, e.g., treating compounds of formula (6) with triethylsilane in the presence of a Lewis acid such as boron trifluoride in a chloronated solvent, followed by suitable conditions to remove the protecting group, or hydrogenating compounds of formula (6) under standard conditions, would yield compounds of formula I(a). Compounds of formula (7) may be generated from compounds of formula (5), (5') or (6) under suitable reaction conditions. Such conditions may involve treating compounds of formula (5) or (5') or (6) with a base such as, e.g., 1,8-diazobicyclo[5.4.0]undec-7-ene in a suitable solvent such as N,N-dimethylformamide at about 140° C. Other solvents such as toluene or N-methylpyrrolidinone may also be useful for this purpose. Subjection of compounds of formula (7) to standard hydrogenation conditions, e.g., hydrogen gas and palladium on charcoal in ethanol, yields compounds of the general formula I(a) when the protecting group was benzyl. Where W is a protecting group, compounds of formula I(b) can be formed by treating compounds of formula (7) to standard conditions that will be obvious to those with skill in the art. Compounds of formula I(b) can in turn be converted to compounds of formula I(a) by standard hydrogenation conditions, such as described above. Compounds I(a) and I(b) fall within the scope of formula I.

Referring to Scheme 2 as an example of a more specific scheme, compounds of formula (8) can be prepared starting with compound (1), which is commercially available (Aldrich Chemical Co.). Conversion to compounds of formula (8) can occur under standard conditions, for instance where the protecting group is benzyl, condensation can occur between compound (1) and benzyl alcohol with the removal of water using Dean-Stark apparatus. Condensation of compounds of formula (8) with compounds of formula (9) may occur using standard techniques, for instance, treatment of compounds of formula (8) with a base such as lithium diisopropylamide in an ethereal solvent followed by the addition of a compound of formula (9) would give compounds of formula (10). Treatment of compounds of formula (10) with a suitable brominating reagent, such as N-bromosuccinimide in a chlorinated solvent at about room temperature, can give compounds of formula (11). Compounds of formula (12) may then be generated from compounds of formula (11) under suitable reaction conditions. Such conditions may involve treating compounds of formula

(11) with a base such as 1,8-diazobicyclo[5.4.0]undec-7-ene in a suitable solvent such as N, N-dimethylformamide at about 140° C. Subjection of compounds of formula (12) to standard hydrogenation conditions, e.g., hydrogen gas and palladium on charcoal in an ethanol/tetrahydrofuran mixture, yields compounds of the general formula I(c) when the protecting group was benzyl. Compounds of formula I(d) may then be obtained by subjecting compounds of formula I(c) to acidic conditions. Compounds of formulae I(c) and I(d) both fall within the scope of formula I.

It will be appreciated by those of skill in the art that in the processes described above, the functional groups of intermediate compounds may need to be protected. The use of protecting groups is well-known in the art, and is fully described, among other places, in: *Protecting Groups in Organic Chemistry*, J. W. F. McOmie, (ed.), 1973, Plenum Press; and in: *Protecting Groups in Organic Synthesis, 2$^{nd}$ edition*, T. W. Greene & P. G. M. Wutz, 1991, Wiley-Interscience, which are incorporated herein by reference in their entirety.

Resorcinol derivatives prepared according to the process described herein are useful for all of the purposes previously described for these types of compounds. For example, resorcinol derivatives useful as skin-lightening agents or for other cosmetic purposes can be prepared according to the process of the present invention.

Where resorcinol derivatives prepared according to the present invention are useful as skin-lightening agents, these may be used to treat disorders of human pigmentation, including solar and simple lentigines (including age/liver spots), melasma/chloasma and postinflammatory hyperpigmentation. Such compounds reduce skin melanin levels by inhibiting the production of melanin, whether the latter is produced constitutively or in response to UV irradiation (such as sun exposure), and typically by inhibition of the enzyme tyrosinase. Active skin-lightening compounds prepared according to the present invention can be used to reduce skin melanin content in non-pathological states so as to induce a lighter skin tone, as desired by the user, or to prevent melanin accumulation in skin that has been exposed to UV irradiation. They can also be used in combination with skin peeling agents (including glycolic acid or trichloroacetic acid face peels) to lighten skin tone and prevent repigmentation. The appropriate dose regimen, the amount of each dose administered, and specific intervals between doses of the active compound will depend upon the particular active compound employed, the condition of the patient being treated, and the nature and severity of the disorder or condition being treated. Preferably, the active compound is administered in an amount and at an interval that results in the desired treatment of or improvement in the disorder or condition being treated.

An active compound prepared according to the process of the present invention can also be used in combination with sun screens (UVA or UVB blockers) to prevent repigmentation, to protect against sun or UV-induced skin darkening or to enhance their ability to reduce skin melanin and their skin bleaching action. An active compound prepared according the process of the present invention can also be used in combination with retinoic acid or its derivatives or any compounds that interact with retinoic acid receptors and accelerate or enhance the invention's ability to reduce skin melanin and skin bleaching action, or enhance the invention's ability to prevent the accumulation of skin melanin. An active compound prepared according to the present invention can also be used in combination with 4-hydroxyanisole.

The active compounds prepared according to the process of the present invention can also be used in combination with ascorbic acid, its derivatives and ascorbic-acid based products (such as magnesium ascorbate) or other products with an anti-oxidant mechanism (such as resveratrol) which accelerate or enhance their ability to reduce skin melanin and their skin bleaching action.

Skin-lightening active compounds prepared according to the present invention are generally administered in the form of pharmaceutical compositions comprising at least one of the compounds of formula (I), together with a pharmaceutically acceptable vehicle or diluent. Such compositions are generally formulated in a conventional manner utilizing solid or liquid vehicles or diluents as appropriate for topical administration, in the form of solutions, gels, creams, jellies, pastes, lotions, ointments, salves, aerosols and the like.

Examples of vehicles for application of the active compounds of this invention include an aqueous or water-alcohol solution, an emulsion of the oil-in-water or water-in-oil type, an emulsified gel, or a two-phase system. Preferably, the compositions according to the invention are in the form of lotions, creams, milks, gels, masks, microspheres or nanospheres, or vesicular dispersions. In the case of vesicular dispersions, the lipids of which the vesicles are made can be of the ionic or nonionic type, or a mixture thereof.

In a skin-lightening composition comprising a resorcinol derivative prepared according to the process of the present invention, the concentration of the resorcinol derivative is generally between 0.01 and 10%, preferably between 0.1 and 10%, relative to the total weight of the composition.

A skin-lightening resorcinol derivative prepared according to the present invention can be conveniently identified by its ability to inhibit the enzyme tyrosinase, as determined by any standard assay, such as those described below.

1. Tyrosinase (DOPA Oxidase) Assay Using Cell Lysate

Human melanoma cell line, SKMEL 188 (licensed from Memorial Sloan-Kettering), is used in the cell lysate assay and the screen. In the assay, compounds and L-dihydroxyphenylalanine (L-DOPA) (100 µg/ml) are incubated with the cell lysates containing human tyrosinase for 8 hrs before the plates are read at 405 nm. Potency of the compounds in DOPA oxidase assay is correlated very well with that in tyrosine hydroxylase assay using $^3$H-tyrosine as a substrate.

2. Melanin Assay in Human Primary Melanocytes

Compounds are incubated with human primary melanocytes in the presence of α-melanocyte stimulating hormone (α-MSH) for 2–3 days. Cells are then lysed with sodium hydroxide and sodium dodecyl sulfate (SDS) and melanin signals are read at 405 nm. Alternatively, $^{14}$C-DOPA is added to the cells in combination with tyrosinase inhibitors and acid-insoluble $^{14}$C-melanin is quantitated by a scintillation counter. $IC_{50}$'s reflect the inhibitory potency of the compounds in the new melanin synthesis that was stimulated by α-MSH.

3. Tyrosine Kinase Assay (TK)

TK assays can be performed using purified tyrosine kinase domains of c-met, erb-B2, or IGF-r. A specific antibody against phosphorylated tyrosine residue is used in the assay. Colorimetric signals are generated by horseradish peroxidase, which is conjugated to the antibody.

4. Human Skin Equivalent Model

A mixture of human melanocytes and keratinocytes is grown in an air-liquid interphase. This tissue culture forms a three dimensional structure that histologically and microscopically resembles the human skin epidermis. Test compounds are added on top of the cells to mimic topical drug application. After incubation with the compounds (10 μM) for 3 days, the cells are washed extensively and lysed for DOPA oxidase assay.

5. IL-1 Assay (Interleukin-1 Assay)

An IL-1α ELISA assay (R&D system) can be used to evaluate the effect of compounds on IL-1 secretion in a human skin equivalent model. IL-1α is a pro-inflammatory cytokine and plays a role in UV-induced skin inflammation.

6. In Vivo Study

Black or dark brown guinea pigs with homogeneous skin color can be used in this study. A solution of the test compound of formula I (5% in ethanol:propylene glycol, 70:30) and the vehicle control are applied to the animals twice daily, 5 days per week for 4–8 weeks. Using this assay, depigmentation can be determined by subtracting the light reflectance of untreated skin from the light reflectance of treated skin.

The present invention is illustrated by the following examples. It will be understood, however, that the invention is not limited to the specific details of these examples. Melting points are uncorrected. Proton nuclear magnetic resonance spectra (400 MHz $^1$H NMR) were measured for solutions in $d_6$-DMSO, CDCl$_3$, or $d_4$-MeOH, and peak positions are expressed in parts per million (ppm) downfield from tetramethylsilane (TMS). The peak shapes are denoted as follows: s, singlet; d, doublet; t, triplet; q, quartet, m, multiplet, b, broad.

The following examples are illustrative only, and are not intended to limit the scope of the present invention.

EXAMPLES

Intermediate 1

3-(Benzyloxy)-2-cyclohexen-1-one

To a round bottomed flask equipped with magnetic stirrer and Dean Stark apparatus was added 1,3-cyclohexanedione (70.0 g, 624 mmol), toluene (500 ml), p-toluenesulfonic acid monohydrate (1.68 g, 8.83 mmol) and benzyl alcohol (65.6 g, 606 mmol). The resulting solution was heated under reflux for 2 hr. The reaction mixture was cooled to room temperature and washed with saturated aqueous sodium carbonate solution (4×50 ml). The organic layer was washed with brine (50 ml), dried over magnesium sulfate, filtered and concentrated in vacuo, affording a brown oil which crystallised upon standing. The crude crystalline material was slurried in isopropyl ether (100 ml) and stirred at 0° C. for 2 hr. The mixture was filtered and the crystalline material was washed with ice cold isopropyl ether (3×100 ml) followed by cold petroleum ether (100 ml). The resulting solid was dried overnight under reduced pressure to furnish the title compound (85.3 g, 68%). m/z (ES$^+$) 203 (M+H$^+$).

Intermediate 2

(±)-3-(Benzyloxy)-6-(8-hydroxy-1,4-dioxaspiro[4.5] dec-8-yl)-2-cyclohexen-1-one

To a round bottomed flask equipped with magnetic stirrer was added anhydrous tetrahydrofuran (600 ml) and diisopropylamine (38.1 ml, 272 mmol). The stirred solution was cooled to −78° C. and n-butyl lithium (113.4 ml, 272 mmol, 2.4 M in hexanes) was added dropwise via syringe in 20 ml portions. The resulting yellow solution was stirred for 35 min at −78° C., then 3-(benzyloxy)-2-cyclohexen-1-one (50.0 g, 248 mmol) was added as a solution in anhydrous tetrahydrofuran (100 ml). The solution was stirred for 1 hr prior to the addition of cyclohexane-1,4-dione monoethylene ketal (38.7 g, 248 mmol) as a solution in anhydrous tetrahydrofuran (100 ml). The solution was stirred for 2 hr at −78° C., then allowed to warm slowly to room temperature over 1 hr. Saturated aqueous ammonium chloride (80 ml) was added, followed by dichloromethane (700 ml) and the mixture was stirred until no solids remained. The layers were separated and the aqueous phase extracted with dichloromethane (2×100 ml). The combined organic layers were washed with brine (50 ml), dried over magnesium sulfate, then concentrated in vacuo. Trituration of the resulting solid with methanol afforded the title compound (78.4 g, 88%). m/z (ES$^+$) 359 (M+H$^+$).

Intermediate 3

(±)-1-(Benzyloxy)-6-bromo-3-(1,4-dioxaspiro[4.5] dec-8-yl)-2-oxabicyclo[2.2.2]octan-5-one A round bottomed flask equipped with magnetic stirrer was charged with (±)-3-(benzyloxy)-6-(8-hydroxy-1,4-dioxaspiro[4.5]dec-8-yl)-2-cyclohexen-1-one (78.4 g, 219 mmol) and dichloromethane (600 ml). To the stirred solution was added N-bromosuccinimide (40.9 g, 230 mmol) in one portion, followed by aqueous hydrobromic acid (3 drops, 48% aqueous solution). The resulting solution was stirred at room temperature for 2 hr, then poured into a separating funnel containing aqueous sodium metablsulfite solution (150 ml) and dichloromethane (200 ml) and the funnel was shaken vigorously. The layers were separated and the organic layer was washed with brine (200 ml), dried over magnesium sulfate, filtered, then concentrated in vacuo to give a solid. Trituration with methanol (500 ml) afforded the title compound (82.8 g, 86%) as a white solid. m/z (ES$^+$) 437 and 439 [(1:1), M+H$^+$].

Intermediate 4

5-(Benzyloxy)-2-(1,4-dioxaspiro[4.5]dec-7-en-8-yl) phenol

A round bottomed flask was charged with (±)-1-(benzyloxy)-6-bromo-3-(1,4-dioxaspiro[4.5]dec-8-yl)-2-oxabicyclo[2.2.2]octan-5-one (36 g, 82.4 mmol) and anhydrous N,N-dimethylformamide (300 ml). To the stirred solution was added 1,8-diazabicyclo[5.4.0]undec-7-ene (13.6 ml, 90.6 mmol) in one portion before heating to 140° C. for 19 hr with vigorous stirring. The reaction mixture was allowed to cool to room temperature and most of the solvent was removed under reduced pressure. The remaining oil was partitioned between dichloromethane (500 ml) and water (100 ml), and the layers were separated. The organic phase was washed with water (2×100 ml) followed by brine (100 ml). The organic phase was dried over magnesium sulfate, filtered and concentrated in vacuo to afford a brown solid which was adsorbed onto silica gel. Purification via flash column chromatography (SiO$_2$, dichloromethane then ethyl acetate/petroleum ether, 3:7, v/v) furnished an off white solid which was slurried in methanol (150 ml). The slurry was stirred for 20 min, filtered and washed with methanol (50 ml). The title compound (18.2 g, 65%) was isolated as a white solid after removal of excess solvent under reduced pressure. m/z (ES$^+$) 339(M+H$^+$).

Example 1

4-(1,4-Dioxaspiro[4.5]dec-8-yl)-1,3-benzenediol

A round bottomed flask equipped with magnetic stirrer was charged with 5-(benzyloxy)-2-(1,4-dioxaspiro[4.5]dec- 7-en-8-yl)phenol (14.5 g, 42.8 mmol) and tetrahydrofuran (50 ml). The stirred mixture was gently heated until a solution formed, after which the solution was allowed to cool to room temperature. Ethanol (100 ml) and palladium (4.54 g, 10% on activated carbon) were added sequentially. The reaction vessel was then evacuated, placed under a hydrogen atmosphere and stirred vigorously for 24 hr. The reaction mixture was filtered through a celite plug, washing with ethyl acetate. The filtrate was concentrated in vacuo to give an off white solid. The crude solid was slurried in dichloromethane (200 ml), then collected on a sinter, affording the title compound (10.2 g, 95%) as a white solid. m/z(ES$^+$)251(M+H$^+$).

Example 2

4-(2,4-Dihydroxyphenyl)cyclohexanone

A round bottomed flask equipped with magnetic stirrer was charged with 4-(1,4-dioxaspiro[4.5]dec-8-yl)-1,3-benzenediol (11.3 g, 45.2 mmol), acetone (250 ml) and water (50 ml). To the stirred solution was added pyridinium p-toluenesulfonate (1.14 g, 4.52 mmol) in one portion and the reaction mixture was then heated under reflux for 8 hr. After allowing the reaction mixture to cool to room temperature, most of the acetone was removed in vacuo and the remaining mixture was partitioned between ethyl acetate (200 ml) and water (50 ml). The aqueous layer was extracted with ethyl acetate (3×50 ml) and the combined organic layers were washed with brine (30 ml), dried over magnesium sulfate, filtered and concentrated under reduced pressure to afford an off-white powder. After washing the powder with dichloromethane (100 ml) and removal of excess solvent under reduced pressure, the title compound (9.30 g, 100%) was obtained as an off-white powder. m/z (ES$^+$) 207 (M+H$^+$); $\delta_H$(CD$_3$OD) 1.84–1.97 (2H, m), 2.15–2.23 (2H, m), 2.36–2.45 (2H, m), 2.58–2.68 (2H, m), 3.39 (1H, tt), 6.26 (1H, dd), 6.34 (1H, d), 6.96 (1H, d).

All patents, patent applications, and publications cited above are incorporated herein by reference in their entirety.

The present invention is not to be limited in scope by the specific embodiments described herein, which are intended as single illustrations of individual aspects of the invention, and functionally equivalent methods and components are within the scope of the invention. Indeed, various modifications of the invention, in addition to those shown and described herein will become apparent to those skilled in the art from the foregoing description. Such modifications are intended to fall within the scope of the appended claims.

What is claimed is:

1. A compound having the structure of formula (4),

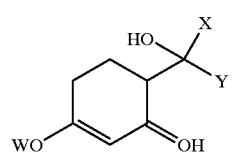

(4)

wherein W is hydrogen or a protecting group; and wherein X and Y are taken together with the carbon to which they are attached to form a (C$_4$–C$_8$)cycloalkyl ring or (C$_5$–C$_8$)cycloalkenyl ring, provided that the (C$_4$–C$_8$) cycloalkyl ring or (C$_5$–C$_8$)cycloalkenyl ring is not aromatic;

and wherein the (C$_4$–C$_8$)cycloalkyl ring or (C$_5$–C$_8$) cycloalkenyl ring is optionally substituted by one to three independently selected groups Z, where Z is selected from the group consisting of cyano; halo; (C$_1$–C$_6$)alkyl; aryl; (C$_2$–C$_9$)heterocycloalkyl; (C$_2$–C$_9$) heteroaryl; aryl(C$_1$–C$_6$)alkyl-; =O; =CHO(C$_1$–C$_6$) alkyl; amino; hydroxy; (C$_1$–C$_6$)alkoxy; aryl(C$_{-C6}$) alkoxy-; (C$_1$–C$_6$)acyl; (C$_1$–C$_6$)alkylamino-; aryl (C$_1$–C$_6$)alkylamino-; amino(C$_1$–C$_6$)alkyl-; (C$_1$–C$_6$) alkoxy-CO—NH—; (C$_1$–C$_6$)alkylamino-CO—; (C$_2$–C$_6$)alkenyl; (C$_2$–C$_6$)alkynyl; hydroxy(C$_1$–C$_6$) alkyl-; (C$_1$–C$_6$)alkoxy(C$_1$–C$_6$)alkyl-; (C$_1$–C$_6$)acyloxy (C$_1$–C$_6$)alkyl-; nitro; cyano(C$_1$–C$_6$)alkyl-; halo(C$_1$–C$_6$) alkyl-; nitro(C$_1$–C$_6$)alkyl-; trifluoromethyl; trifluoromethyl(C$_1$–C$_6$)alkyl-; (C$_1$–C$_6$)acylamino-; (C$_1$–C$_6$)acylamino(C$_1$–C$_6$)alkyl-; (C$_1$–C$_6$)alkoxy (C$_1$–C$_6$)acylamino-; amino(C$_1$–C$_6$)acyl-; amino (C$_1$–C$_6$)acyl(C$_1$–C$_6$)alkyl-; (C$_1$–C$_6$)alkylamino (C$_1$–C$_6$)acyl-; ((C$_1$–C$_6$)alkyl)$_2$amino(C$_1$–C$_6$)acyl-; —CO$_2$R$^2$; —(C$_1$–C$_6$)alkyl-CO$_2$R$^2$; —C(O)N(R$^2$)$_2$; —(C$_1$–C$_6$)alkyl-C(O)N(R$^2$)$_2$; R$^2$ON=; R$_2$ON= (C$_1$–C$_6$)alkyl-; R$^2$ON=CR$^2$(C$_1$–C$_6$)alkyl-; —NR$^2$ (OR$^2$); —(C$_1$–C$_6$)alkyl-NR$^2$(OR$^2$); —C(O)(NR$^2$OR$^2$); —(C$_1$–C$_6$)alkyl-C(O)(NR$^2$OR$^2$); —S(O)$_m$R$^2$; wherein each R$^2$ is independently selected from hydrogen, (C$_1$–C$_6$)alkyl, aryl, or aryl(C$_1$–C$_6$)alkyl-; R$^3$C(O)O—, wherein R$^3$ is (C$_1$–C$_6$)alkyl, aryl, or aryl(C$_1$–C$_6$)alkyl-; R$^3$C(O)O—(C$_1$–C$_6$)alkyl-; R$^4$R$^5$N—C(O)—O—; R$^4$R$^5$NS(O)$_2$—; R$^4$R$^5$NS(O)$_2$(C$_1$–C$_6$)alkyl-; R$^4$S(O)$_2$ R$^5$N—; R$^4$S(O)$_2$R$^5$N(C$_1$–C$_6$)alkyl-; wherein m is 0, 1, or 2, and R$^4$ and R$^5$ are each independently selected from hydrogen or (C$_1$–C$_6$)alkyl; —C(=NR$^6$)(N(R$^4$)$_2$); —(C$_1$–C$_6$)alkyl-C(=NR$^6$)(N(R$^4$)$_2$wherein R$^6$ represents OR$^2$ or R$^2$ wherein R$^2$ is defined as above; —OC(O)aryl(C$_1$–C$_6$)alkyl; —NH(C$_1$–C$_6$)alkyl; aryl (C$_1$–C$_6$)alkyl-HN—; and a ketal.

2. The compound of claim 1 having the structure of formula (4a),

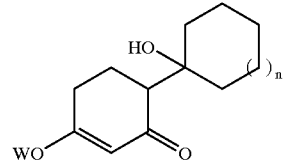

(4a)

wherein W is as defined above, and n is 0, 1, 2 or 3.

3. The compound of claim 2, having the structure of formula (4b) or (4c)

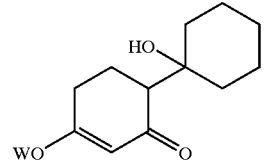

(4b)

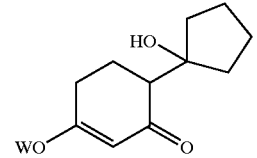

(4c)

wherein W is as defined above.

4. The compound of claim 1, having the structure of formula (4d),

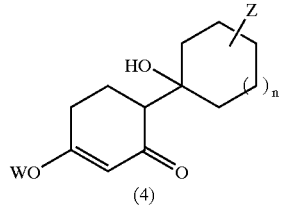

(4d)

wherein W and Z are as defined above, and wherein n is 0, 1, 2 or 3.

5. The compound of claim 4, having the structure of formula (4e) or (4f),

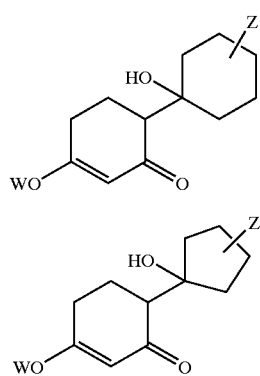

(4e)

(4f)

wherein W and Z are as defined above.

6. The compound of claim 1, having the structure of formula (4g),

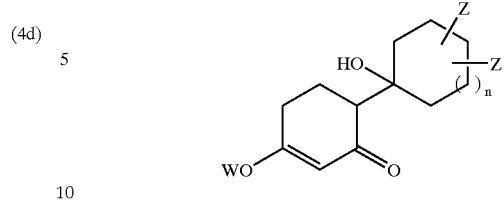

(4g)

wherein W and Z are as defined above, and wherein n is 0, 1, 2 or 3.

7. The compound of claim 6, having the structure of formula (4h) or (4i),

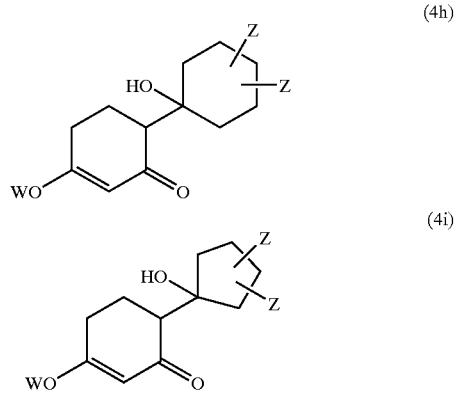

(4h)

(4i)

wherein W and Z are as defined above, and wherein n is 0, 1, 2 or 3.

* * * * *